US00PP31135P3

(12) United States Plant Patent
Moen

(10) Patent No.: US PP31,135 P3
(45) Date of Patent: Nov. 26, 2019

(54) ***GERBERA* PLANT NAMED 'GARSWLOVE'**

(50) Latin Name: *Gerbera hybrida*
Varietal Denomination: Garswlove

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 0 days.

(21) Appl. No.: 15/999,869

(22) Filed: Aug. 23, 2018

(65) Prior Publication Data

US 2019/0069463 P1 Feb. 28, 2019

Related U.S. Application Data

(60) Provisional application No. 62/605,740, filed on Aug. 24, 2017.

(51) Int. Cl.
*A01H 5/02* (2018.01)
*A01H 6/14* (2018.01)

(52) U.S. Cl.
USPC ..... Plt./357
CPC ..... *A01H 6/1456* (2018.05)

(58) Field of Classification Search
USPC ..... Plt./357
See application file for complete search history.

(56) References Cited

PUBLICATIONS

UPOV hit on a *Gerbera* plant named 'Garswlove', QZ PBR 20180240, filed Jan. 19, 2018.*
UPOV hit on a *Gerbera* plant named 'Garswlove', JP PBR 33165, filed Aug. 8, 2018.*

* cited by examiner

*Primary Examiner* — Anne Marie Grunberg
(74) *Attorney, Agent, or Firm* — C. A. Whealy

(57) ABSTRACT

A new and distinct cultivar of *Gerbera* plant named 'Garswlove', characterized by its compact, broadly upright and uniformly mounding plant habit; dense and bushy appearance; numerous inflorescences with bright red-colored ray florets; upright and strong scapes; and good garden performance and relatively tolerant to cold temperatures.

1 Drawing Sheet

Botanical designation: *Gerbera hybrida.*
Cultivar denomination: 'GARSWLOVE'.

BACKGROUND OF THE INVENTION

The present invention relates to a new and distinct cultivar of *Gerbera* plant, botanically known as *Gerbera hybrida* and hereinafter referred to by the cultivar name 'Garswlove'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination made during the spring of 2013 in De Kwakel, The Netherlands of a proprietary selection of *Gerbera hybrida* identified as code number 13T1040, not patented, as the female, or seed, parent with a proprietary selection of *Gerbera hybrida* identified as code number 13T1077, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the summer of 2014.

Asexual reproduction of the new *Gerbera* plant by cuttings in a controlled environment in De Kwakel, The Netherlands since the autumn of 2014 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garswlove'. These characteristics in combination distinguish 'Garswlove' as a new and distinct *Gerbera* plant:

1. Compact, broadly upright and uniformly mounding plant habit.
2. Dense and bushy appearance.
3. Numerous inflorescences with bright red-colored ray florets.
4. Upright and strong scapes.
5. Good garden performance and relatively tolerant to cold temperatures.

Plants of the new *Gerbera* differ primarily from plants of the female parent selection in the following characteristics:

1. Plants of the new *Gerbera* have smaller inflorescences than plants of the female parent selection.
2. Inflorescences of plants of the new *Gerbera* smaller ray florets than inflorescences of plants of the female parent selection.

3. Plants of the new *Gerbera* have lighter red-colored ray florets than plants of the female parent selection.

Plants of the new *Gerbera* differ primarily from plants of the male parent selection in ray floret shape as ray florets of plants of the new *Gerbera* have finely emarginate to finely praemorse apices whereas ray florets of plants of the male parent selection have deeply emarginate to deeply praemorse apices. In addition, plants of the new *Gerbera* have dark green-colored leaves whereas plants of the male parent selection have green-colored leaves tinged with anthocyanin (reddish purple).

Plants of the new *Gerbera* can be compared to plants of the *Gerbera hybrida* 'Garglow Imp', disclosed in U.S. Plant Pat. No. 26,784. Plants of the new *Gerbera* differ from plants of 'Garglow Imp' in the following characteristics:

1. Leaves of plants of the new *Gerbera* are narrower than leaves of plants of 'Garglow Imp'.
2. Inflorescences of plants of the new *Gerbera* are smaller than inflorescences of plants of 'Garglow Imp'.
3. Ray florets of plants of the new *Gerbera* are bright red in color whereas ray florets of plants of 'Garglow Imp' are bright orange in color.
4. Peduncles of plants of the new *Gerbera* are somewhat shorter than peduncles of plants of 'Garglow Imp'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garswlove' grown in a container.

DETAILED BOTANICAL DESCRIPTION

The aforementioned photograph and following observations and measurements describe plants grown during the winter until early summer in 15-cm containers in a glass-covered greenhouse in De Kwakel, The Netherlands and under cultural practices typical of commercial garden *Gerbera* production. During the production of the plants, day temperatures ranged from 16° C. to 20° C. and night temperatures ranged from 15° C. to 17° C. Plants were six months old when the photograph was taken and seven months old when the detailed description was taken. In the following description, color references are made to The Royal Horticultural Society Colour Chart, 2015 Edition, except where general terms of ordinary dictionary significance are used.

Botanical classification: *Gerbera hybrida* 'Garswlove'.

Parentage:

*Female, or seed, parent*.—Proprietary selection of *Gerbera hybrida* identified as code number 13T1040, not patented.

*Male, or pollen, parent*.—Proprietary selection of *Gerbera hybrida* identified as code number 13T1077, not patented.

Propagation:

*Type*.—By cuttings and meristem culture.

*Time to initiate roots, by cuttings, summer and winter*.—About 3.5 weeks at temperatures about 20° C.

*Time to initiate roots, by tissue culture, summer and winter*.—About 2.5 to 3 weeks at temperatures about 20° C.

*Time to produce a rooted young plant, by cuttings, summer and winter*.—About 3.5 weeks at temperatures about 20° C. to 26° C.

*Time to produce a rooted young plant, by tissue culture, summer and winter*.—About five to six weeks at temperatures about 20° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; compact and uniformly mounding plant habit; upright, broadly spreading and roughly flattened globular in shape; numerous leaves arranged in basal rosettes; dense and bushy habit; inflorescences held above the foliar plane on erect and strong basal scapes; moderately vigorous growth habit; moderate growth rate.

*Plant height, soil level to top of foliar plane*.—About 27.6 cm.

*Plant height, soil level to top of inflorescences*.—About 39.6 cm.

*Plant width*.—About 42.1 cm.

Leaf description:

*Arrangement*.—Alternate, simple.

*Length*.—About 17.4 cm.

*Width*.—About 6.9 cm.

*Shape*.—Oblanceolate to narrowly obovate; runcinate; slightly curved.

*Apex*.—Obtuse.

*Base*.—Acuminate.

*Margin*.—Coarsely and irregularly angulate; sinuses medium in depth and divergent; slightly to moderately undulate.

*Texture and luster, upper surface*.—Moderately to densely pubescent; slightly rugose; slightly glossy.

*Texture and luster, lower surface*.—Moderately to densely pubescent, slightly rugose; matte.

*Venation pattern*.—Pinnate.

*Color*.—Developing leaves, upper surface: Close to between 137A and 141A. Developing leaves, lower surface: Close to 137B. Fully expanded leaves, upper surface: Close to NN137A; venation, close to 144A. Fully expanded leaves, lower surface: Close to NN137D and 147B; venation, close to 144A.

*Petioles*.—Length: About 10.4 cm. Diameter: About 4 mm. Texture and luster, upper and lower surfaces: Densely pubescent; moderately glossy. Strength: Moderate to strong. Color, upper surface: Close to 144A; proximally, close to 183A. Color, lower surface: Close to 144B; proximally, close to 183A.

Inflorescence description:

*Appearance*.—Composite inflorescence form with oblanceolate-shaped ray florets; solitary inflorescences borne on upright and strong scapes and held above the foliar plane; ray and disc florets arranged acropetally on a capitulum; inflorescences face upright to slightly outwardly.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about four weeks on the plant; inflorescences persistent.

*Quantity of inflorescences*.—Freely flowering habit with about 13 open and developing inflorescences per plant at one time.

*Inflorescence buds*.—Height: About 1 cm. Diameter: About 1.8 cm. Shape: Roughly globular. Texture and luster: Densely pubescent; matte. Color: Close to 137B to 137C; immature ray florets, close to 150B.

*Inflorescence size*.—Diameter: About 7.7 cm. Depth (height): About 2.6 cm. Diameter of disc: About 2.5 cm. Receptacle height: About 3 mm. Receptacle diameter: About 5 mm. Receptacle color: Close to 145C.

*Ray florets*.—Quantity and arrangement: About 50 per inflorescence arranged in about two whorls. Orientation: About 60° from vertical; distally, curving downwardly. Length: About 3.5 cm. Width: About 7 mm. Shape: Oblanceolate. Apex: Finely emarginate to finely praemorse. Base: Narrowly cuneate. Margin: Entire. Texture and luster, upper surface: Smooth, glabrous; velvety; matte. Texture and luster, lower surface: Smooth, glabrous; moderately velvety; slightly carinate; matte. Color: When opening, upper surface: Close to 42A. When opening, lower surface: Close to 166D. Fully opened, upper surface: Close to 44A to 44B; venation, close to 44A to 44B; color does not fade with development. Fully opened, lower surface: Close to 35A, 35B and 39A; venation, close to 35A, 35B and 39A; color does not fade with development.

*Disc florets*.—Quantity and arrangement: About 300 massed at center of receptacle in about eleven whorls. Length: About 1.1 cm. Width: About 3.5 mm. Shape: Tubular with upper two narrow free lobes and one broader free lobe. Apex: Acute; upper 35%, free. Base: Lower 65%, fused. Margin, free lobes: Entire. Texture, upper surface: Smooth, glabrous; moderately velvety; matte. Texture, lower surface: Smooth, glabrous; slightly velvety; slightly glossy. Color: When opening, inner surface: Close to 42A; proximally, close to 151D. When opening, outer surface: Close to 35B; proximally, close to 151D. Fully opened, inner surface: Close to 45B; proximally, close to 151D. Fully opened, outer surface: Close to 39A; proximally, close to 151D.

*Pappus*.—Quantity of hairs per floret: About 60. Length: About 7 mm. Diameter: Less than 1 mm. Texture and luster: Soft; matte. Color: Close to 162D; distally, lighter than 162D.

*Phyllaries*.—Quantity and arrangement: About 60 per inflorescence arranged in about three whorls. Length: About 1.4 cm. Width (at base): About 3 mm. Shape: Ligulate. Apex: Narrowly acute. Base: Cuneate. Margin: Entire. Texture and luster, upper surface: Smooth, glabrous; moderately glossy. Texture and luster, lower surface: Moderately to densely pubescent; matte. Color, upper surface: Close to 143C. Color, lower surface: Close to 137A; fading distally to close to 138B.

*Scapes*.—Length: About 34.7 cm. Diameter: Proximally, about 5 mm; distally, about 3.5 mm. Strength: Moderately strong. Angle: About 15° from vertical. Texture and luster: Densely pubescent; moderately glossy. Color: Close to 144A; proximally, close to 183A; distally, close to 146A.

*Reproductive organs*.—Androecium (present on disc florets only): Quantity per floret: Five. Filament length: About 1.5 mm. Filament color: Close to 150C. Anther shape: Ligulate; basifixed. Anther size: About 2 mm by 0.3 mm. Anther color: Close to 9B. Pollen amount: Scarce to moderate. Pollen color: Close to 13B. Gynoecium (present only on ray and disc florets): Quantity per floret: One. Pistil length: About 1.1 cm. Stigma diameter: About 0.5 mm. Stigma shape: Cleft. Stigma color: Close to 11D. Style length: About 1 cm. Style color: Close to 56C to 56D. Ovary color: Close to 157D.

*Seeds and fruits*.—To date, seed and fruit production has not been observed on plants of the new *Gerbera*.

Disease & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate high temperatures about 35° C. and to be cold hardy to USDA Hardiness Zone 7.

It is claimed:

1. A new and distinct *Gerbera* plant named 'Garswlove' as illustrated and described.

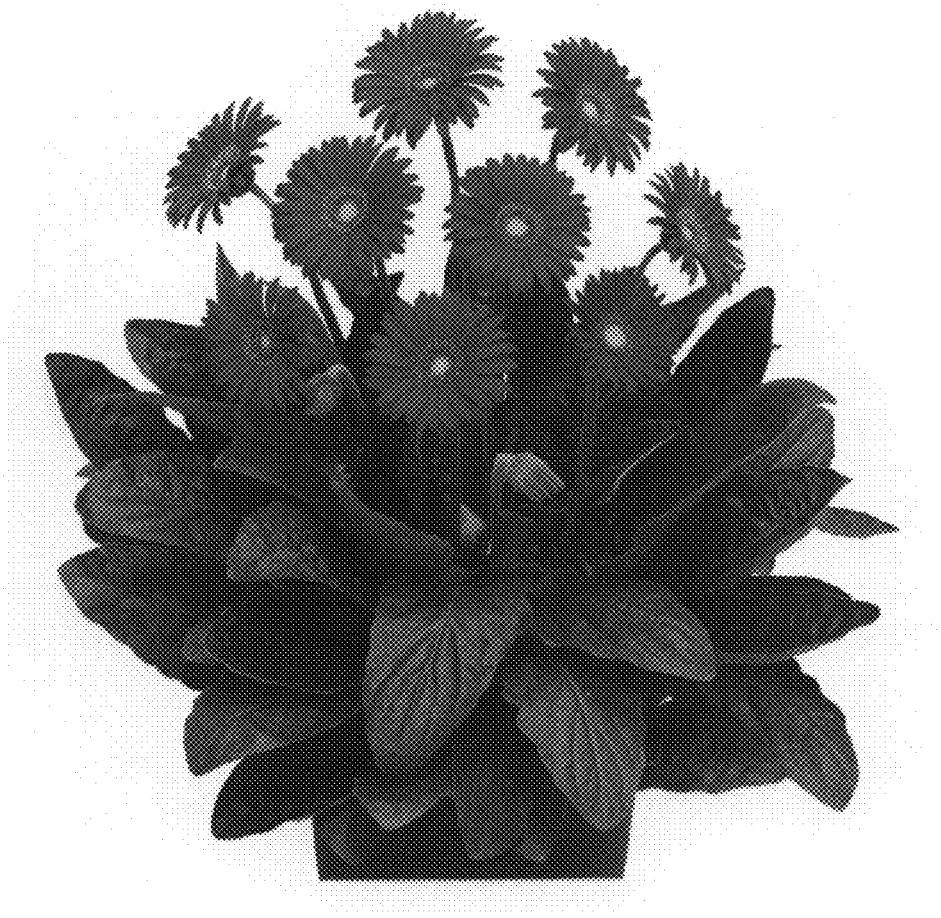

* * * * *